United States Patent
Hastings (10) Patent No.: US 7,253,404 B2
(45) Date of Patent: Aug. 7, 2007

(54) MEDIAN FILTER FOR LIQUID CHROMATOGRAPHY-MASS SPECTROMETRY DATA

(75) Inventor: Curtis Hastings, San Mateo, CA (US)

(73) Assignee: PPD Biomarker Discovery Sciences, LLC, Wilmington, NC (US)

( * ) Notice: Subject to any disclaimer, the term of this patent is extended or adjusted under 35 U.S.C. 154(b) by 0 days.

(21) Appl. No.: 11/173,937

(22) Filed: Jul. 1, 2005

(65) Prior Publication Data

US 2006/0097154 A1 May 11, 2006

Related U.S. Application Data

(63) Continuation of application No. 10/935,562, filed on Sep. 7, 2004, now Pat. No. 6,936,814, which is a continuation of application No. 09/994,575, filed on Nov. 27, 2001, now Pat. No. 6,787,761.

(60) Provisional application No. 60/314,996, filed on Aug. 24, 2001, provisional application No. 60/253,178, filed on Nov. 27, 2000.

(51) Int. Cl.
*H01J 49/00* (2006.01)
(52) U.S. Cl. .................................. 250/282; 702/30
(58) Field of Classification Search ................ 250/282, 250/281; 702/30, 27, 22
See application file for complete search history.

(56) References Cited

U.S. PATENT DOCUMENTS

| | | | |
|---|---|---|---|
| 3,552,865 A | 1/1971 | Leung et al. |
| 3,690,836 A | 9/1972 | Buissiere et al. |
| 3,997,298 A | 12/1976 | McLafferty et al. |
| 3,999,047 A | 12/1976 | Green |
| 4,405,235 A | 9/1983 | Rossiter |
| 4,426,451 A | 1/1984 | Columbus |
| 4,643,570 A | 2/1987 | Machler et al. |
| 4,752,888 A | 6/1988 | Yoshihara |
| 4,761,381 A | 8/1988 | Blatt et al. |
| 4,786,813 A | 11/1988 | Svanberg et al. |
| 4,844,617 A | 7/1989 | Kelderman et al. |
| 4,963,498 A | 10/1990 | Hillman et al. |
| 5,072,382 A | 12/1991 | Kamentsky |
| 5,091,652 A | 2/1992 | Mathies et al. |

(Continued)

FOREIGN PATENT DOCUMENTS

DE 19829094 1/2000

(Continued)

OTHER PUBLICATIONS

Aach et al., 2001, "Aligning Gene Expression Time Series With Time Warping Algorithms", Bioinformatics 17:495-508.

(Continued)

*Primary Examiner*—Kiet T. Nguyen (57) ABSTRACT

High-intensity, spiked noise is reduced in chromatography-mass spectrometry data by applying a nonlinear filter such as a moving median filter to the data. The filter is applied to individual mass chromatograms, plots of ion abundance versus retention time for each detected mass-to-charge ratio, and the filtered chromatograms are combined to form a filtered total ion current chromatogram. Standard linear filters are not effective for reducing noise in liquid chromatography-mass spectrometry (LC-MS) data because they assume a normal distribution of noise. LC-MS noise, however, is not normally distributed.

20 Claims, 9 Drawing Sheets

U.S. PATENT DOCUMENTS

| | | | |
|---|---|---|---|
| 5,119,315 A | 6/1992 | Kemp et al. | |
| 5,127,730 A | 7/1992 | Brelje et al. | |
| 5,192,980 A | 3/1993 | Dixon et al. | |
| 5,239,178 A | 8/1993 | Derndinger et al. | |
| 5,274,240 A | 12/1993 | Mathies et al. | |
| 5,304,810 A | 4/1994 | Amos | |
| 5,377,003 A | 12/1994 | Lewis et al. | |
| 5,412,208 A | 5/1995 | Covey et al. | |
| 5,430,542 A | 7/1995 | Shepherd | |
| 5,446,532 A | 8/1995 | Yamazaki | |
| 5,453,505 A | 9/1995 | Lee et al. | |
| 5,456,252 A | 10/1995 | Vari et al. | |
| D366,938 S | 2/1996 | Shartle et al. | |
| 5,492,833 A | 2/1996 | Rodriguez et al. | |
| 5,523,573 A | 6/1996 | Hanninen et al. | |
| 5,532,873 A | 7/1996 | Dixon | |
| 5,547,849 A | 8/1996 | Baer et al. | |
| 5,556,764 A | 9/1996 | Sizto et al. | |
| 5,578,832 A | 11/1996 | Trulson et al. | |
| 5,585,246 A | 12/1996 | Dubrow et al. | |
| 5,592,402 A | 1/1997 | Beebe et al. | |
| 5,627,041 A | 5/1997 | Shartle | |
| D382,648 S | 8/1997 | Shartle et al. | |
| 5,658,735 A | 8/1997 | Lee | |
| D383,852 S | 9/1997 | Shartle et al. | |
| 5,672,869 A | 9/1997 | Windig et al. | |
| 5,682,038 A | 10/1997 | Hoffman | |
| 5,687,964 A | 11/1997 | Stephan et al. | |
| 5,689,110 A | 11/1997 | Dietz et al. | |
| 5,692,220 A | 11/1997 | Diamond et al. | |
| 5,710,713 A | 1/1998 | Wright et al. | |
| D391,373 S | 2/1998 | Shartle | |
| 5,713,364 A | 2/1998 | Debaryshe et al. | |
| 5,726,751 A | 3/1998 | Altendorf et al. | |
| 5,734,058 A | 3/1998 | Lee | |
| 5,736,410 A | 4/1998 | Zarling et al. | |
| 5,739,000 A | 4/1998 | Bierre et al. | |
| 5,741,411 A | 4/1998 | Yeung et al. | |
| D395,708 S | 6/1998 | Shartle | |
| 5,795,729 A | 8/1998 | Lee | |
| 5,814,820 A | 9/1998 | Dong et al. | |
| 5,832,826 A | 11/1998 | Mack et al. | |
| 5,867,610 A | 2/1999 | Lee et al. | |
| 5,871,946 A | 2/1999 | Lucas et al. | |
| 5,885,841 A | 3/1999 | Higgs, Jr. et al. | |
| 5,910,287 A | 6/1999 | Cassin et al. | |
| 5,912,134 A | 6/1999 | Shartle | |
| 5,932,428 A | 8/1999 | Dubrow et al. | |
| 5,962,238 A | 10/1999 | Sizto et al. | |
| 5,981,180 A | 11/1999 | Chandler et al. | |
| 5,995,989 A | 11/1999 | Gedcke et al. | |
| 6,002,986 A | 12/1999 | Mito | |
| 6,008,490 A | 12/1999 | Kato | |
| 6,008,896 A | 12/1999 | Sabsabi et al. | |
| 6,017,693 A | 1/2000 | Yates | |
| 6,059,724 A | 5/2000 | Campell | |
| 6,063,338 A | 5/2000 | Pham et al. | |
| 6,066,216 A | 5/2000 | Ruppel, Jr. | |
| 6,072,624 A | 6/2000 | Dixon et al. | |
| 6,091,492 A | 7/2000 | Strickland et al. | |
| 6,093,573 A | 7/2000 | Beamer et al. | |
| 6,104,945 A | 8/2000 | Modell et al. | |
| 6,112,161 A | 8/2000 | Dryden et al. | |
| 6,133,046 A | 10/2000 | Clerc | |
| 6,134,002 A | 10/2000 | Stimson et al. | |
| 6,138,117 A | 10/2000 | Bayardo | |
| 6,147,344 A | 11/2000 | Annis et al. | |
| 6,200,532 B1 | 3/2001 | Wu et al. | |
| 6,207,955 B1 | 3/2001 | Wells et al. | |
| 6,215,892 B1 | 4/2001 | Douglass et al. | |
| 6,229,603 B1 | 5/2001 | Coassin et al. | |
| 6,229,635 B1 | 5/2001 | Wulf | |
| 6,232,114 B1 | 5/2001 | Coassin et al. | |
| 6,236,945 B1 | 5/2001 | Simpson et al. | |
| 6,253,162 B1 | 6/2001 | Jarman et al. | |
| 6,278,794 B1 | 8/2001 | Parekh et al. | |
| 6,334,099 B1 | 12/2001 | Grace et al. | |
| 6,376,843 B1 | 4/2002 | Palo | |
| 6,377,842 B1 | 4/2002 | Pogue et al. | |
| 6,388,788 B1 | 5/2002 | Harris et al. | |
| 6,391,649 B1 | 5/2002 | Chait et al. | |
| 6,400,487 B1 | 6/2002 | Harris et al. | |
| 6,421,612 B1 | 7/2002 | Agrafiotis et al. | |
| 6,449,584 B1 | 9/2002 | Bertrand et al. | |
| 6,514,767 B1 | 2/2003 | Natan | |
| 6,526,299 B2 | 2/2003 | Pickard | |
| 6,552,784 B1 | 4/2003 | Dietz et al. | |
| 6,590,204 B2 | 7/2003 | Baranov | |
| 6,603,537 B1 | 8/2003 | Dietz et al. | |
| 6,620,591 B1 | 9/2003 | Dunlay et al. | |
| 6,625,546 B2 | 9/2003 | Sepetov et al. | |
| 6,642,059 B2 | 11/2003 | Chait et al. | |
| 6,646,271 B2 | 11/2003 | Yokokawa et al. | |
| 6,687,395 B1 | 2/2004 | Dietz et al. | |
| 6,753,966 B2 | 6/2004 | Von Rosenberg | |
| 6,787,761 B2 * | 9/2004 | Hastings | 250/282 |
| 6,800,860 B2 | 10/2004 | Dietz et al. | |
| 6,835,927 B2 | 12/2004 | Becker et al. | |
| 6,858,435 B2 | 2/2005 | Chervet et al. | |
| 6,873,915 B2 | 3/2005 | Hastings | |
| 6,936,814 B2 * | 8/2005 | Hastings | 250/282 |
| 6,937,330 B2 | 8/2005 | Dietz et al. | |
| 6,950,185 B1 | 9/2005 | Da Silva et al. | |
| 6,962,818 B2 | 11/2005 | Schneider et al. | |
| 6,979,830 B2 | 12/2005 | Dietz et al. | |
| 2001/0019829 A1 | 9/2001 | Nelson et al. | |
| 2002/0049152 A1 | 4/2002 | Nock et al. | |
| 2002/0053545 A1 | 5/2002 | Greef | |
| 2002/0095419 A1 | 7/2002 | Parce | |
| 2002/0102610 A1 | 8/2002 | Townsend et al. | |
| 2002/0123055 A1 | 9/2002 | Estell et al. | |
| 2002/0141051 A1 | 10/2002 | Vogt et al. | |
| 2003/0087322 A9 | 5/2003 | Aebersold et al. | |
| 2004/0257576 A1 | 12/2004 | Kirsch et al. | |
| 2006/0000984 A1 | 1/2006 | Wolleschensky et al. | |

FOREIGN PATENT DOCUMENTS

| | | |
|---|---|---|
| EP | 0296136 | 12/1988 |
| EP | 0421736 | 4/1991 |
| EP | 0681177 | 11/1995 |
| EP | 0969283 | 1/2000 |
| GB | 1407247 | 9/1975 |
| WO | WO-97 43732 | 11/1997 |
| WO | WO-98 16661 | 4/1998 |
| WO | WO-00 67017 | 11/2000 |
| WO | WO-00 70340 | 11/2000 |
| WO | WO-01 35266 | 5/2001 |
| WO | WO-01 44269 | 6/2001 |
| WO | WO-2088819 | 11/2002 |

OTHER PUBLICATIONS

Baumgarth et al., 2000, "A Practical Approach to Multicolor Flow Cytometry for Immunophenotyping," J. Immunol Methods, 243(1-2):77-97.

Beavis et al., 1996, "Allo-7: A New Fluorescent Tandem Dye for Use in Flow Cytometry," Cytometry 24(4):390-395.

Berlier et al., 2003, "Quantitative Comparison of Long-Wavelength Alexa Fluor Dyes to Cy Dyes: Fluorescence of the Dyes and Their Bioconjugates," J. Histochem Cytochem, 51(12):1699-1712.

Beu et al., 2004, "Broadband Phase Correction of FT-ICR Mass Spectra via Simultaneous Excitation and Detection," Anal. Chem., v. 76, pp. 5756-5761.

Breen et al., 2000, "Automatic Poisson Peak Harvesting for High Throughput Protein Identification", Electrophoresis, 21:2243-2251.

Bruchez et al., 1998, "Semiconductor Nanocrystals as Fluorescent Biological Labels," Science, 281(5385):2013-2016.

Bryant et al., 2001, "Principal Component Analysis of Mass Spectra of Peptides Generated from the Tryptic Digestion of Protein Mixtures," Rapid Commun. Mass Spectrom. 15:418-427.

Bucknall et al., 2002, "Practical Quantitative Biomedical Applications of MALDI-TOF Mass Spectrometry", J. Am. Soc. Mass Spectrom. 13:1015.

Bylund, 2001, "Chemometric Tools for Enhanced Performance in Liquid Chromatography—Mass Spectrometry," Acta Univ. Ups., Comprehensive Summaries of Uppsala Dissertations from the Faculty of Science and Technology, 07. 47 pp. Uppsala. ISBN 91-554-4946-8.

Bylund et al.,2002, "Chromatographic Alignment by Warping and Dynamic Programming as a Pre-Processing Tool for PARAFAC Modellling of Liquid Chromatography-Mass Spectrometry Data", J. of Chromatography A., 961:237-244.

Cagney et al., 2002, "De Non Peptide Sequencing and Quantitative Profiling of Complex Protein Mixtures Using Mass-Coded Abundance Tagging", Nat. Biotech. 20:163.

Caprioli et al., 1972, "Use of Stable Isotopes", Biochem. Appl. Mass Spectrom. 27:735-776.

Chace, 2001, "Mass Spectrometry in the Clinical Laboratory", Chem. Rev. 101: 445-477.

Chelius et al., 2002, "Quantitative Profiling of Proteins in Complex Mixtures Using Liquid Chromatography and Mass Spectrometry", J. Proteome Res. 1:317-323.

Coons, 1961, "The Beginnings of Immunofluorescence," J. Immunol, 87:499-503.

De Rosa et al., 2001, "11-Color, 13-Parameter Flow Cytometry: Identification of Human Naive T-Cells by Phenotype, Function, and T-cell Receptor Diversity," Nat. Med., 7(2):245-248.

De Rosa et al., 2003, "Beyond Six Colors: a New Era in Flow Cytometry," Nature Medicine, vol. 9, No. 1, pp. 112-117.

Dietz et al., 1996, "Volumetric Capillary Cytometry: A New Method for Absolute Cell Enumeration", Cytometry 23:177-186.

do Lago et al.,1995, "Applying Moving Median Digital Filter to Mass Spectrometry and Potentiiometric Titration", Anal. Chim. Acta, 310: 281-288.

Elavathil et al., 1996, "Reproducibility of DNA Ploidy and S-Phase Values from Parraffin-Embedded Tissue", Analytical and Quantitative Cytology and Histology, vol. 18, No. 4, 316-322.

Felinger, 1998, "Data Analysis and Signal Processing in Chromatographpy," Data Handling in Science and Technology, vol. 21,pp. 149-152.

Fiehn et al., 2000, "Metabolite Profiling for Plant Functional Genomics", Nat. Biotech. 18:1157-1161.

Glazer et al., 1983, "Fluorescent Tandem Phycobiliprotein Conjugates- Emission Wavelength Shifting by Energy Transfer," Biophys J, 43(3):383-386.

Grung et al., 1995, "Retention Time Shift Adjustments of Two-Way Chromatograms Using Bessel's Inequality", Analytica Chimica Acta, 304:57-66.

Gygi et al.,1999, "Quantitative Analysis of Complex Protein Mixtures Using Isotope-Coded Affinity Tabs", Nat. Biotech., 17:994-999.

Ha et al., 1999, "Single-molecule Fluorescence Spectroscopy of Enzyme Conformational Dynamics and Cleavage Mechanism," Biophysics, vol. 96, pp. 893-898.

Hamberg et al., 1973, "Quantitative Studies on Prostaglandin Synthesis in Man", Anal. Biochem., 55:368.

Hastings et al., 2002, "New Algorithms for Processing and Peak Detection in Liquid Chromatography/Mass Spectrometry Data", Rapid Communications in Mass Spectrometry, 16(5):462-467.

Holst, 1998, "CCD Arrays, Camera and Displays", 2d Ed., JCD Publishing and SPIE Optical Engineering Press, pp. i-xxiii.

Jeanmaire et al., 1977, "Surface Raman Spectroelectrochemistry Part 1: Heterocyclic, Aromatic, and Aliphatic Amines Adsorbed on the Anodized Silver Electrode," J. Electroanal. Chem., 84:1-20.

Ji et al., 2000, "Strategy for Qualitative and Quantitative Analysis in Proteomics Based on Signature Peptides", J. Chromat. B 745:197.

Kamentsky, 2001, "Laser Scanning Cytometry," Methods Cell. Biol., 63:51-87.

Kantor et al., 1996, "FACS Analysis of Leukocytes," In: Herzenberg LA, Weir DM, Herzenberg LA, Blackwell C, editors, Weir's Handbook of Experimental Immunology, 5th ed. vol. 2. Cambridge, MA: Blackwell Science; p. 49.1-49.13.

Kantor, 2002, "Comprehensive Phenotyping and Biological Marker Discovery," Disease Markers, 18(2):91-97.

Kantor et al., 2004, "Immune Systems Biology: Immunoprofiling of Cells and Molecules," BioTechniques, 36(3):520-524.

Kantor et al., 2004, "Biomarker Discovery by Comprehensive Phenotyping for Autoimmune Diseases," Clinical Immunology, 111:186-195.

Kassidas et al., 1998, "Synchronization of Batch Trajectories Using Dynamic Time Warping", AIChE Journal 44(4):864-875.

Kast et al., 2003, "Noise Filtering Techniques for Electrospray Quadrupole Time of Fluid Mass Spectra," J. Am. Soc. Mass Spectrom., v. 14, pp. 766-776.

Koradi et al., 1998, "Automated Peak Picking and Peak Integration in Macromolecular NMR Spectra Using AUTOPSY", J. Magn. Reson., 135:288-297.

Mahalingam, 1996, "Analysis of Surface Density of Expression of Molecules by Flow Cytometry", Cytometry 24:190.

Moore et al., 1993, "Median Filitering for Removal of Low-Frequency Background Drift," Anal.Chem., 65: 188-191.

Mujumdar et al., 1996, "Cyanine-Labeling Reagents: Sulfoindocyanine Succinimidyl Esters," Bioconjug Chem, 7, 356-362.

Nelson et al., 1995, "Mass Spectrometric Immunoassay", Anal. Chem. 67:1153.

Nielsen et al., 1998, "Aligning of Single and Multiple Wavelength Chromatographic Profiles for Chemometric Data Analysis Using Correlation Optimised Warping", J. of Chromatography A. 805:17-35.

Norton et al., 2000, "Cell Enumeration and Characterization in Microvolume Laser Scanning Cytometry: A Multicolor Image Processing Package," IBOS Society of Photo-Optical Instrumentation Engineers, p. 20-30.

Oda et al., 1999, "Accurate Quantitation of Protein Expression and Site-Specific Phosphorylation", Proc. Natl. Acad. Sci. USA 96:6591.

Oi et al., 1982, "Fluorescent Phycobiliprotein Conjugates for Analyses of Cells and Molecules," J. Cell Biol, 93(3):981-6.

Panchuk-Voloshina et al., 1999, "Alexa Dyes, A Series of New Fluorescent Dyes That Yield Exceptionally Bright, Photostable Conjugates," J. Histochem Cytochem, 47(9):1179-88.

Perez et al., 2002, "Simultaneous Measurement of Multiple Active Kinase States Using Polychromatic Flow Cytometry," Nat Biotechnol, 20(2):155-162.

Perez et al., 2004, "Flow Cytometric Analysis of Kinase Signaling Cascades," Methods Mol Biol, 263:67-94.

Perou et al., 2000, "Molecular Portraits of Human Breast Tumours", Nature, vol. 406, pp. 747-752.

Pinajian et al., 1953, "The Isotope Dilution Procedure of Analysis", J. Am. Phar. Assoc., 301-304.

Pravdova et al., 2002, "A Comparison of Two Algorithms for Warping of Analytical Signals", Analytica Chimica Acta 456:77-92.

Prazen et al., Jan. 15, 1998, "Standardization of Second-Order Chromatographic/Spectroscopic Data for Optimum Chemical Analysis", Anal. Chem. 70:218-225.

Proceedings of SPIE V, 1997, "Ultrasensitive Biochemical Diagnostics II", The International Society for Optical Engineering, Feb. 10-12, San Jose, CA.

Roederer et al., 1996, "Cy7PE and Cy7APC: Bright New Probes for Immunofluorescence," Cytometry, 24(3):191-7.

Sakoe et al., 2002, "Dynamic Programming Algorithm Optimization for Spoken Word Recognition" IEEE Transactions on Acoustics, Speech and Signal Processing ASSP26(1):43-49.

Schoonjans et al., 2000, "Use of Mass Spectrometry for Assessing Similarity/Diversity of Natural Products with Unknown Chemical Structures", J. Pharm. & Biomed. Analysis, 21:1197-1214.

Stein, 1999, "An Integrated Method for Spectrum Extraction and Compound Identification from Gas Chromatography/Mass Spectrometry Data", J Am Soc Mass Spectrum 10:770-781.

Stewart et al., 1999, "Four Color Compensation", Cytometry, vol. 38, No. 4, 161-175.

Van Duyne, 1979, "Laser Excitation of Raman Scattering from Adsorbed Molecules on Electrode Surfaces," In: Moore CB, editor, Chemical and Biochemical Applications of Lasers, pp. 101-185.

Voyksner et al., 1999, "Investigating the use of an Octupole Ion Guide for Ion Storage and High-pass Mass Filtering to Improve the Quatitative Performance of Electro spray Ion Trap Mass Spectrometry," Rapid Commun. Mass Spectrom., v. 13, pp. 1427-1437.

Waggoner et al., 1993, "PE-CY5- A New Fluorescent Antibody Label for Three-color Flow Cytometry with a Single Laser," Ann N Y Acad Sci, 677:185-93.

Walton et al., 2000, "Microvolume Laser Scanning Cytometry Platform for Biological Marker Discovery," Proc.SPIE-Int.Soc.Opt. Eng., 3926:192-201.

Wang et al.,1987, "Time-Warping Algorithm Applied to Chromatographic Peak Matching Gas Chromatography/Fourier Transform Infrared/Mass Spectrometry", Analytical Chemistry 59:649-654.

Wang et al., 2003, "Quantification of Proteins and Metabolites by Mass Spectrometry Without Isotopic Labeling or Spiked Standards", Anal. Chem. 75:4818.

Watson et al., 2003, "Lighting up Cells with Quantum Dots," Biotechniques, 34(2):296-300, 302-3.

Windig et al., 1996, "A Noise and Background Reduction Method for Component Detection in Liquid Chromatography/Mass Spectrometry", Anal. Chem., 68: 3602-3606.

Wu et al., 2003, "Immunofluorescent Labeling of Cancer Marker Her2 and Other Cellular Targets with Semiconductor Quantum Dots," Nat Biotechnol, 21(1):41-6.

Zuck et al., 1999, "Ligand-receptor Binding Measured by Laser-scanning Imaging," Proc. Natl. Acad. Sci., 96(20):11122-11127.

Doering et al., 2002, "Single-Molecule and Single-Nanoparticle SERS: Examining the Roles of Surface Active Sites and Chemical Enhancement," J. Phys. Chem. B., 106:311-317.

Nie et al., 1997, "Probing Single Molecules and Single Nanoparticles by Surface-Enhanced Raman Scattering," Science, New Series, 275(5303):1102-1106.

Nie et al., 1997, "Probing Single Molecules and Single Nanoparticle by Surface-Enhanced Raman Scattering," Science, New Series, 275(5303):1102-1106.

Tibbe et al., 1999, "Optical Tracking and Detection of Immunomagnetically Selected and Aligned Cells," Nature Biotechnology, 17:1210-1213.

Wyant et al., 2001, "Whole Blood Microvolume Laser Scanning Cytometry for Monitoring Resting and Activated Platelets," Platelets, 12:309-318.

Constantino, et al., 2001 "Single-Molecule Detection Using Surface-Enhanced Resonance Raman Scattering and Langmuir-Blodgett Monolayers," Anal. Chem., vol. 73, pp. 3674-3678.

Ha, T., 2001, "Single-Molecule Fluorescence Resonance Energy Transfer," Methods, 25:78-86.

Rossetti et al., 1982, "Electron-Hole Recombination Emission as a Probe of Surface Chemistry in Aqueous CdS Colloids," J. Phys. Chem., 86:4470-4472.

Kneipp et al., 1999, "Ultrasensitive Chemical Analysis by Raman Spectroscopy," Chem. Rev., 99:2957-2975.

Martens et al., 1999, "A Generic Particle-Based Nonradioactive Homogeneous Multiplex Method for High-Throughput Screening Using Microvolume Fluorimetry," Analytical Biochemistry, 273:20-31.

Mulvaney et al., 2003, "Glass-Coated, Analyte-Tagged Nanoparticles: A New Tagging System Based on Detection with Surface-Enhanced Raman Scattering," Langmuir, 19:4784-4790.

Steigerwald et al., 1988, "Surface Derivatization and Isolation of Semiconductor Cluster Molecules," J. Am. Chem. Soc., 110:3046-3050.

Swartzman et al., 1999, "A Homogeneous and Multiplexed Immunoassay for High-Throughput Screening Using Fluorometric Microvolume Assay Technology," Analytical Biochemistry, 271:143-151.

Mulvaney, et al., 2000 "Raman Spectroscopy," Proc. Anal. Chem., vol. 72, pp. 145R-157R.

* cited by examiner

Prior Art

FIG. 1A

Prior Art

MEDIAN FILTER FOR LIQUID CHROMATOGRAPHY-MASS SPECTROMETRY DATA

RELATED APPLICATIONS

This application is a continuation of patent application Ser. No. 10/935,562, "Median Filter for Liquid Chromatography-Mass Spectrometry Data," filed Sep. 7, 2004, now U.S. Pat. No. 6,936,814, which is a continuation of patent application Ser. No. 09/994,575, "Median Filter for Liquid Chromatography-Mass Spectrometry Data," filed Nov. 27, 2001, now U.S. Pat. No. 6,787,761, which claims the benefit of U.S. Provisional Application 60/253,178, "Informatics System," filed Nov. 27, 2000 and U.S. Provisional Application No. 60/314,996, "Nonlinear Filter For Liquid Chromatography-Mass Spectrometry Data," filed Aug. 24, 2001, all of which are herein incorporated by reference.

FIELD OF THE INVENTION

This invention relates generally to analysis of data collected by analytical techniques such as chromatography and spectrometry. More particularly, it relates to a nonlinear filter such as a moving median filter for noise reduction in mass chromatograms acquired by liquid chromatography-mass spectrometry.

BACKGROUND OF THE INVENTION

Liquid chromatography-mass spectrometry (LC-MS) is a well-known combined analytical technique for separation and identification of chemical mixtures. Chromatography separates the mixture into its constituent components, and mass spectrometry further analyzes the separated components for identification purposes.

In its basic form, chromatography involves passing a mixture dissolved in a mobile phase over a stationary phase that interacts differently with different mixture constituents. Components that interact more strongly with the stationary phase move more slowly and therefore exit the stationary phase at a later time than components that interact more strongly with the mobile phase, providing for component separation. A detector records a property of the exiting species to yield a time-dependent plot of the property, e.g., mass or concentration, allowing for quantification and, in some cases, identification of the species. For example, an ultraviolet (UV) detector measures the UV absorbance of the exiting analytes over time. When liquid chromatography is coupled to mass spectrometry, mass spectra of the eluting components are obtained at regular time intervals for use in identifying the mixture components. Mass spectra plot the abundance of ions of varying mass-to-charge ratio produced by ionizing and/or fragmenting the eluted components. The spectra can be compared with existing spectral libraries or otherwise analyzed to determine the chemical structure of the component or components. Note that LC-MS data are two-dimensional; that is, a discrete data point (intensity) is obtained for varying values of two independent variables, retention time and mass-to-charge ratio (m/z).

Figure 1A:
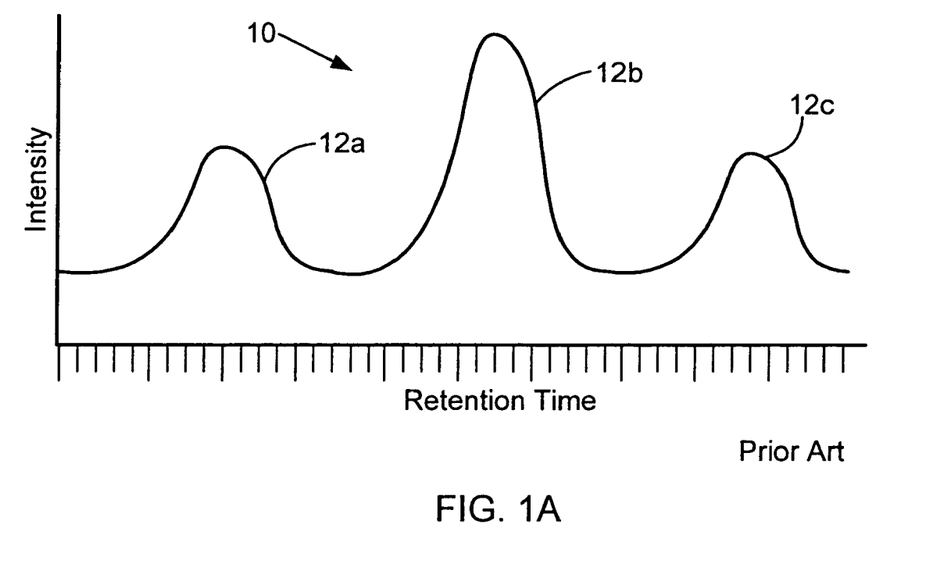
FIGS. 1A-1B are schematic diagrams of a noise-free total ion current chromatogram and a noisy total ion current chromatogram, respectively, as known in the prior art.
Figure 1B:
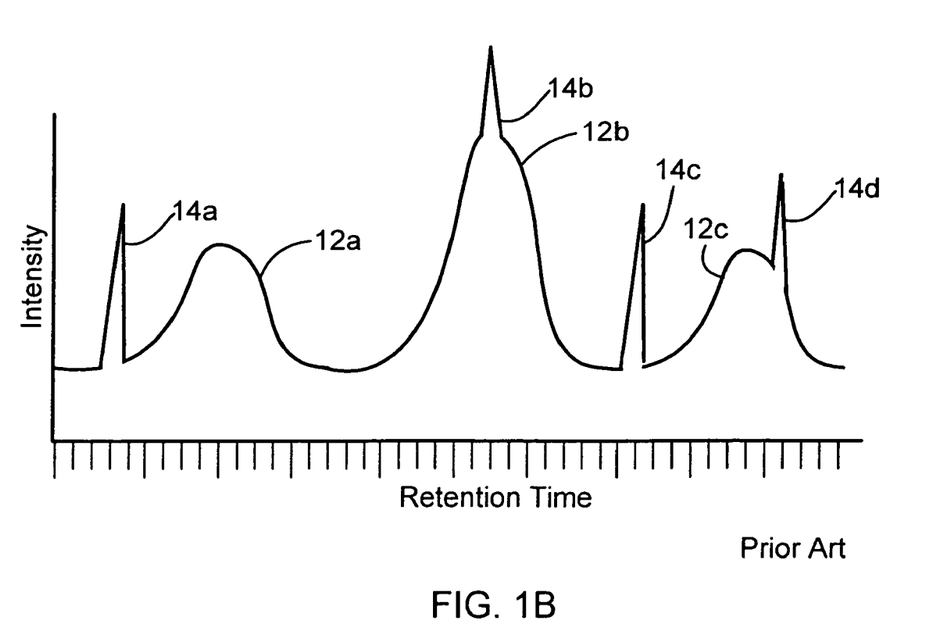

LC-MS data are typically reported by the instrument as a total ion current (TIC) chromatogram, the sum of all detected ions at each scan time. Peaks in the chromatogram represent separated components of the mixture eluting at different retention times. A noise-free chromatogram 10, shown in FIG. 1A, appears as a series of smooth peaks 12a-12c, each extending over multiple scan times. As shown in the TIC chromatogram of FIG. 1B, however, LC-MS data often have high-intensity noise spikes 14a-14d superimposed on the peaks. Although components elute over multiple scans, noise spikes typically do not extend beyond one scan time. If the TIC chromatogram has little noise, an operator can determine the total number of peaks and then examine each peak's corresponding mass spectrum to identify the eluted species. However, as the amount of noise present increases, it becomes more difficult for the operator to distinguish the chromatographic peaks, particularly if the noise level is higher than the signal level. In such cases, the operator is left to examine each individual mass spectrum manually, select the mass-to-charge ratios corresponding to known or likely mixture components, and then assemble a reduced total ion current chromatogram from the selected masses only. Such a procedure is clearly very time consuming. Furthermore, when the mixture contains unknown analytes, the operator cannot confidently determine which mass spectral peaks are noise and which are actual peaks. Thus the only recourse the operator has is to adjust various instrument parameters and repeat the experiment with a different sample, hoping for less noise in the resulting chromatogram.

Because it enables the identification and quantification of hundreds to thousands of analytes in a single injection, LC-MS is currently being used to analyze complex biological mixtures (see, e.g., D. H. Chace et al., "Mass Spectrometry in the Clinical Laboratory," Chem. Rev. 101 (2001): 445-477). Proteomics is a relatively new field that aims to detect, identify, and quantify proteins to obtain biologically relevant information. Both proteomics and metabolomics (the detection, identification, and quantification of metabolites and other small molecules such as lipids and carbohydrates) may facilitate disease mechanism elucidation, early detection of disease, and evaluation of treatment. Recent advances in mass spectrometry have made it an excellent tool for structural determination of proteins, peptides, and other biological molecules. However, proteomics and small molecule studies typically have a set of requirements that cannot be met by manual interpretation of the LC-MS data.

First, these studies require high-throughput analysis of small volumes of biological fluid. Manual data interpretation creates a bottleneck in sample processing that severely limits the number of samples that can be analyzed in a given time period. Furthermore, while large available sample volumes allow an operator to adjust parameters by trial and error to obtain adequate chromatograms and spectra, biological samples are available in such small volumes that it is imperative to extract useful information from all of the available sample. Second, unlike traditional research applications, in which a relatively small amount of data is required, the paradigm of these studies is to acquire enormous amounts of data and then mine the data for new correlations and patterns. Manual data analysis is therefore unfeasible. In addition, biological samples are generally complex mixtures of unknown compounds, and so it is not desirable to extract only known spectra and discard the remaining data, an approach that has been used for studies involving quantification of known compounds in a mixture. Finally, LC-MS instruments produce an enormous amount of data: a single one-hour chromatographic run can produce up to 80 MB of binary data. For storage and subsequent data mining purposes, it is highly desirable to reduce the amount of data to retain information while discarding noise. To satisfy these requirements, a data analysis method is needed that can acquire a large amount of data from low-volume biological mixtures, extract useful information from the resulting noisy data set, and identify unknown compounds from the extracted information. An essential component of such a method is the ability to filter noise accurately so that peaks can be distinguished automatically.

The problem of filtering chromatographic noise has been addressed to various degrees in the prior art. The component detection algorithm (CODA) is an automated method for selecting mass chromatograms with low noise and low background. CODA is described in W. Windig et al., "A Noise and Background Reduction Method for Component Detection in Liquid Chromatography/Mass Spectrometry," *Anal. Chem.*, 68 (1996): 3602-3606. The method computes a smoothed and mean-subtracted version of each mass chromatogram, compares it with the original chromatogram, and calculates a similarity index between the two. Chromatograms whose similarity index exceeds a threshold value are retained and combined to form a reduced total ion chromatogram, while other chromatograms are rejected. CODA has proven very effective at selecting high-quality mass chromatograms. However, it can only accept or reject entire chromatograms based on their noise level, but cannot filter noise from an individual chromatogram. As a result, noisy chromatograms that contain useful information are eliminated, and important peaks may not be detected.

Techniques exist for filtering noise and background from spectrometric data. For example, U.S. Pat. No. 5,995,989, issued to Gedcke et al., describes a filtering method in which an average background level and an average deviation from the background are computed and used to define a local threshold for each data point. Points exceeding the threshold are retained, while points below the threshold are considered to be noise and discarded. The technique described in Gedcke et al. is only effective for noise levels that are substantially below the level of the peaks. For data such as that illustrated in FIG. 1B, high-intensity noise spikes cannot be removed using the disclosed method.

In U.S. Pat. No. 6,112,161, issued to Dryden et al., a method for enhanced integration of chromatography or spectrometry signals is described. A baseline signal is computed from a moving average of the actual signal. The difference between the baseline and actual signal is a baseline-adjusted signal containing peaks and high-frequency noise. An intensity range of the noise is determined, and all signal outside of this range is considered to be peaks, while signal inside this range is considered to be noise. As with the method of Gedcke et al., the method of Dryden et al. can only be used when the noise intensity is substantially lower than the signal intensity. Because LC-MS data often has noise values exceeding the signal values, the method of Dryden et al. is not effective at removing noise from LC-MS data.

A moving median digital filter has been used to remove noise from mass spectrometry and potentiometric titration data, as described in C. L. do Lago et al., "Applying moving median digital filter to mass spectrometry and potentiometric titration," *Anal. Chim. Acta,* 310 (1995): 281-288. Each data point is replaced by the median of the values in a window surrounding the point. With respect to the mass spectrometry data, the filter is applied both to the electron multiplier output, i.e., the ion abundance values, and to the magnetic field sensor, i.e., the mass-to-charge ratio. The method is not, however, applied to two-dimensional data such as LC-MS data. In most cases, state-of-the-art LC-MS instruments do not report the mass spectra as continuous smooth peaks, but rather as centroided data, i.e., single-mass peaks at the average mass value of the true peak. Without centroiding, an unmanageable amount of data would be generated for each spectrum. A moving median filter applied to centroided mass spectral data would remove peaks and noise equally. Because the peak shape is removed in the reported data, filtering or analytical methods cannot be applied to the mass spectra. Moreover, in some cases, one major source of noise, detector noise, can corrupt an entire mass spectrum. If a high fraction of the points in the filter window are corrupted, then a median filter applied to the spectrum cannot remove this noise.

There is still a need, therefore, for a method for removing noise, particularly high-intensity spikes, from chromatographic and spectrometric data such as LC-MS data.

SUMMARY OF THE INVENTION

The present invention provides a method for filtering noisy mass chromatograms in two-dimensional liquid chromatography-mass spectrometry (LC-MS) data. The method can remove noise spikes that have a higher intensity than peaks corresponding to eluted analytes, while essentially retaining the peak intensity and shape. It therefore performs substantially better than conventional linear filters that assume a normal distribution of the noise.

In a method of the invention for characterizing a chemical or biological sample, a series of mass spectra are generated by chromatography (e.g., liquid chromatography) and mass spectrometry. A total ion current (TIC) chromatogram is obtained from the mass spectra, and a median filter is applied to the chromatogram, resulting in a filtered total ion chromatogram with lower noise than the original chromatogram. Preferably, individual chromatograms are generated from the series of mass spectra, and the filter is applied separately to each individual chromatogram. The total ion current chromatogram is then reconstructed from the individual filtered chromatograms. Alternatively, the raw mass spectral data can be compared with the filtered chromatograms and the raw data replaced with the corresponding filtered data if the filtered data has a lower intensity value. The TIC chromatogram can then be assembled from the thresholded raw data. Subsequent to filtering, additional post-acquisition processing steps can be performed, such as applying a component detection algorithm to the filtered data to select relatively noise-free individual chromatograms.

The filter can be any suitable median filter such as a moving median filter or modified median filter, and the method preferably also includes selecting and optimizing one or more parameters of the filter. For example, the parameter can be selected based on the scan rate of the mass spectrometer or on subsequent data analysis, such as peak selection, of the mass spectra.

Also provided by the present invention is a program storage device accessible by a processor and tangibly embodying a program of instructions executable by the processor to perform method steps for the above method.

DETAILED DESCRIPTION OF THE INVENTION

The present invention provides a method for filtering chromatographic and spectrometric data to reduce noise in individual mass chromatograms, thereby facilitating subsequent selection of peaks or high quality chromatograms for component detection. In liquid chromatography-mass spectrometry (LC-MS) or gas chromatography-mass spectrometry (GC-MS) data, the noise intensity is often larger than the intensity of the peaks corresponding to eluted species, making it very difficult to extract meaningful information from the data. The method of the invention is able to reduce substantially such large magnitude noise spikes.

LC-MS noise originates from a variety of sources corresponding to different components of the system. Each physical mechanism of the system contributes its own noise distribution to the final measured ion current. For example, chemical noise results from column bleed, i.e., long-time elution of strongly-adsorbed species at particular mass-to-charge ratios, low-concentration sample contaminants, and detection of the chromatographic mobile phase. In the mass spectrometer, the ion generation, selection, and detection processes all generate noise. Electronic signal processing and analog-to-digital conversion add noise to the acquired data. The noise sources and distributions are not well understood for all components, making it difficult to select an appropriate filter.

Figure 2A:
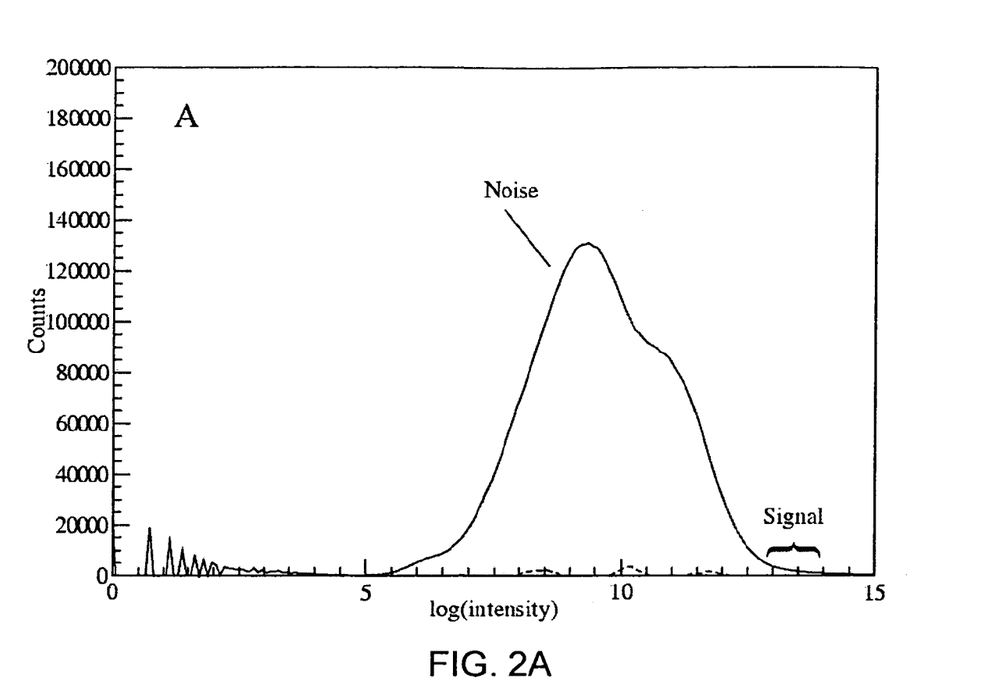
FIGS. 2A-2B are histograms of LC-MS spectral intensities of a five-protein mixture and a high-molecular weight human serum fraction, respectively.
Figure 2B:
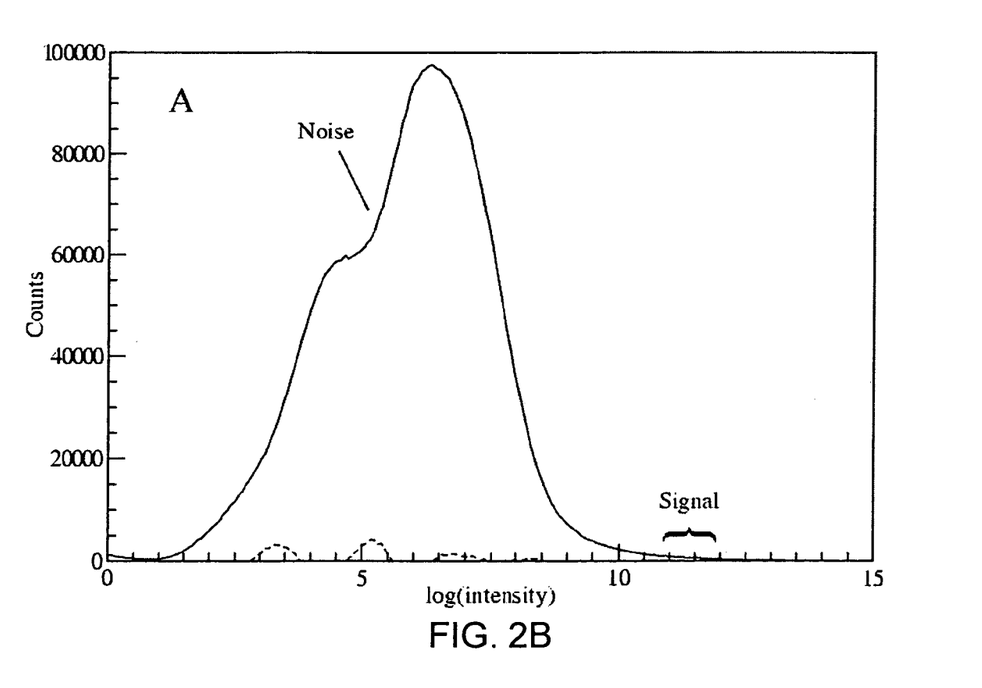

In order to understand the noise distribution in LC-MS data better, the present inventor has prepared histograms of non-normalized intensity distributions of LC-MS spectra of two samples. FIG. 2A is a histogram of log intensity for a tryptic digest of a five-protein mixture (equal amounts by mass of horse myoglobin, bovine RNAse A, bovine serum albumin, bovine cytochrome C, and human hemoglobin). FIG. 2B is a histogram of log intensity for a tryptic digest of a high-molecular weight fraction of human serum produced by ultrafiltration through a 10 kD cutoff membrane. In both cases, the samples were reduced with dithiothreitol and carboxymethylated using iodoacetic acid and sodium hydroxide prior to digestion. The two samples display similar distributions, one at relatively low intensity and the other at higher intensity. In general, the major noise component of LC-MS data is chemical. It is believed that the second distribution, at lower ion current intensities, is associated with electrical noise. Both distributions appear close to normal in the log scale.

In methods of the invention, a digital median filter, a nonlinear filter, is applied to individual mass chromatograms to reduce the noise level. A mass chromatogram is a plot of intensity versus retention time for a particular range of mass-to-charge ratio of detected ions. A nonlinear filter applies a nonlinear function to the data to be filtered. A nonlinear filter such as a median filter is particularly well-suited to LC-MS data because of the noise distribution characteristics of this type of data. As recognized by the present inventor, noise in LC-MS data is not normally distributed in the linear scale, i.e., does not follow a Gaussian distribution. Additionally, empirical study of LC-MS data has revealed that in individual mass chromatograms, noise spikes typically occur over a single scan time only. Standard filtering techniques for LC-MS data use moving average filters, which are linear filters and therefore effective at removing only normally distributed noise. Note that while noise may be correlated in adjacent points along the mass axis of a mass spectrum, it is typically not as highly correlated along the time axis. Thus there is no guarantee that noise reduction methods developed for one of the dimensions can be extended to the other dimension.

Figure 3A:
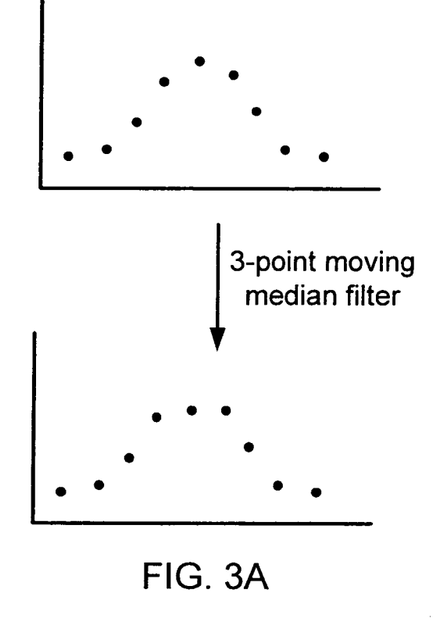
FIGS. 3A-3B illustrate a moving median filter of the invention applied to a chromatogram peak and to a chromatogram noise spike, respectively.
Figure 3B:
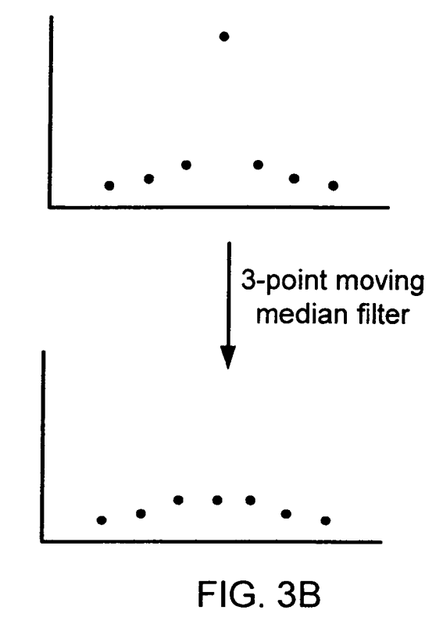

A simple median filter used in the preferred embodiment of the invention is a moving median filter, illustrated in FIGS. 3A-3B. A moving median filter replaces each point with the median of the points in a window of a given size centered on the selected point. For example, a three-point window examines a selected point and the neighboring point on each side of the selected point. Moving median filters are used for noise suppression in image processing but, to the knowledge of the present inventor, have not previously been applied to chromatographic data. FIG. 3A illustrates the application of a three-point moving median filter to a smooth chromatographic peak extending over multiple MS scan times. The top plot is the raw data, and the bottom plot is the filtered data. Points on the peak side slopes are necessarily the median of the three values in the window, and do not change upon application of the filter. The highest point of the peak is replaced by the larger of the two neighboring values. Thus the moving median filter flattens the peak slightly.

Figure 3C:
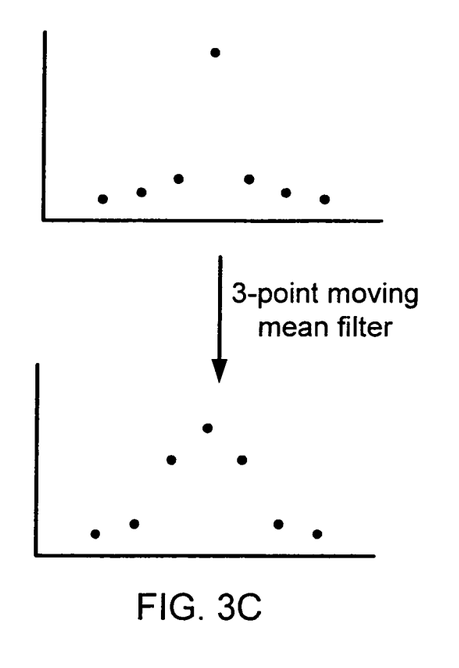
FIG. 3C illustrates a moving average filter applied to a chromatogram noise spike.

FIG. 3B illustrates the effect of the same three-point moving median filter on a single-point noise spike. The points surrounding the spike change little, if at all, but the noise spike is replaced by the higher of its two adjacent points, i.e., is completely removed. FIGS. 3A-3B highlight the benefits of a moving median filter: it removes high-intensity noise spikes while retaining the sharpness of peak edges. In general, the filter removes features narrower than its half-width while retaining features wider than its width. A three-point moving average filter applied to the same noise spike is illustrated in FIG. 3C. In this case, each point is replaced by the mean of itself and its two surrounding points. The points at the edge of the noise spike are increased in value, while the spike itself is reduced significantly, but is still present. If the noise is of larger magnitude than the actual peaks, then the filtered noise is comparable to the peaks, and the filter is not effective in reducing noise.

Figure 4:
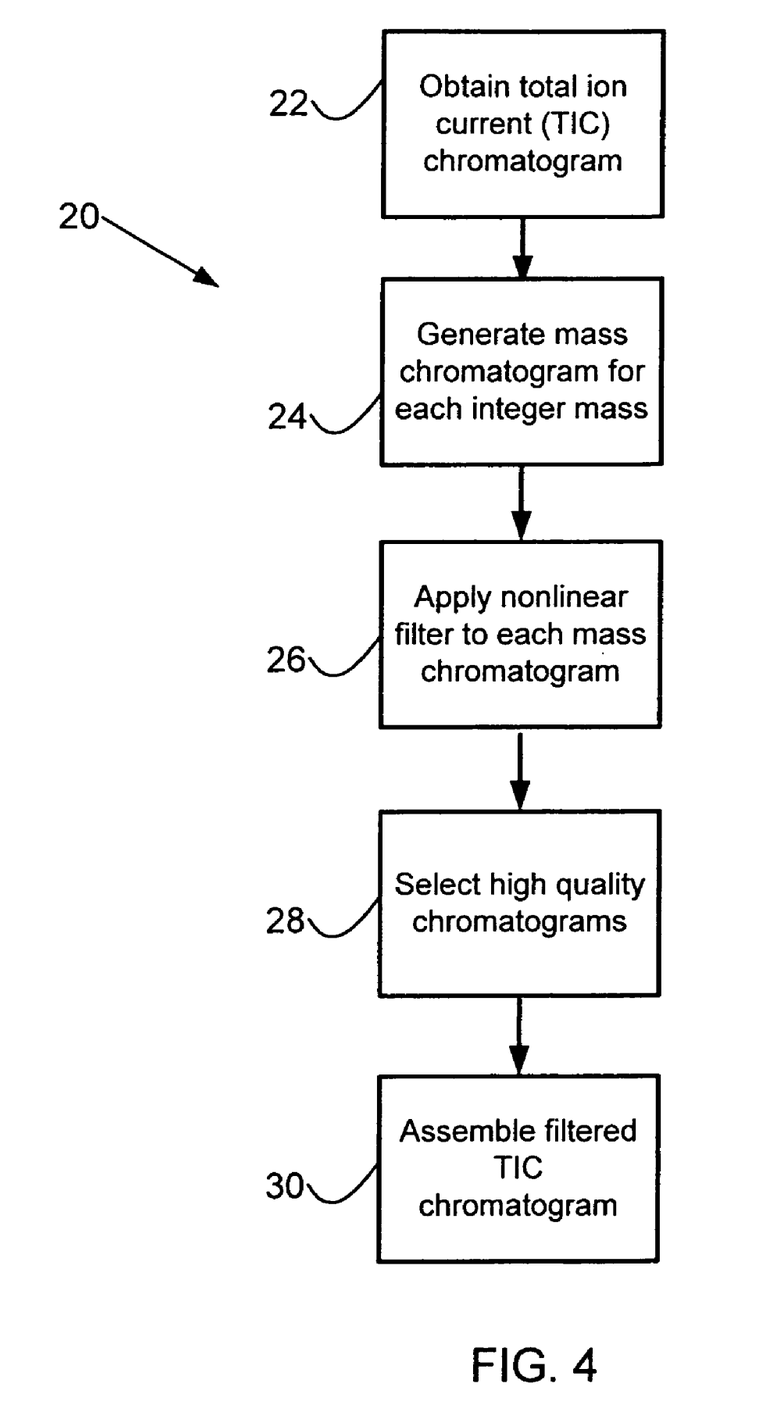
FIG. 4 is a flow diagram of a median filter method of the present invention.

A flow diagram of a method 20 of the invention for reducing noise in LC-MS or GC-MS data is shown in FIG. 4. First, in step 22, the time-dependent mass spectra are acquired. Next, in step 24, a mass chromatogram is generated for each integer mass in the entire set of mass spectra. For example, peaks at masses of 1321.7 and 1322.1 are summed and combined into the mass chromatogram for an integer mass of 1322. Alternatively, data points can be combined into mass ranges that do not necessarily correspond to integer values. In step 26, the median filter is applied to each mass chromatogram generated in step 24.

Next, in an optional step 28, a component selection algorithm such as CODA is applied to the filtered mass chromatograms.

Finally, the filtered mass chromatograms are combined into a reduced or filtered total ion current chromatogram in step 30. One method is simply to sum the intensities at each time point. Alternatively, the raw mass spectral data obtained in step 22 can be thresholded using the filtered chromatograms. To do this, each raw data point is compared with its corresponding point in the filtered chromatograms. Recall that the raw data contain points at non-integer values of mass-to-charge ratio, while the filtered chromatograms contain points corresponding to ranges of mass values. If the intensity value of the raw data exceeds the value of the corresponding filtered point, then the original point is replaced by the filtered value. If not, it is retained.

The method 20 is typically implemented as part of an automated data analysis method for two-dimensional LC-MS or GC-MS. Data filtered according to the present invention may be subjected to, for example, peak recognition algorithms and structural identification algorithms. It is anticipated that the filtered data can be much more successfully analyzed by subsequent algorithms than can unfiltered data. In fact, one of the problems with the CODA method is that it removes noisy chromatograms, thereby also removing any information contained within the chromatograms.

Although the method 20 is best implemented by applying the median filter to the individual mass chromatograms and then combining the filtered chromatograms into a reduced total ion current chromatogram, the filter alternatively can be applied directly to the original total ion current chromatogram. In individual mass chromatograms, noise spikes typically occur over a single scan time only and are therefore effectively filtered using a moving median filter of the invention. In the total ion current chromatogram, however, spikes that occur at different masses but adjacent retention times can effectively merge to extend over multiple scan times and therefore pass the filter.

Figure 5:
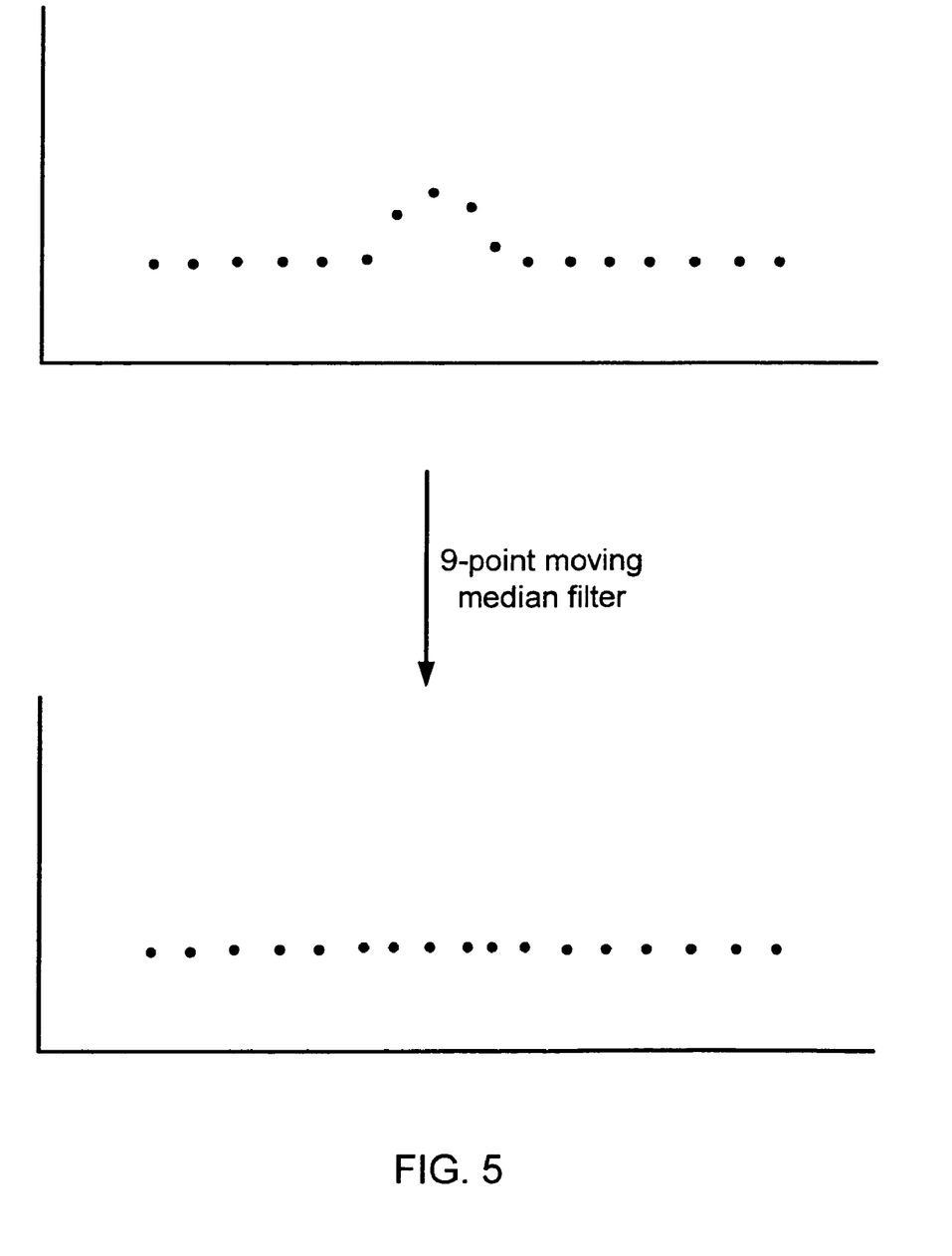
FIG. 5 illustrates the application of a moving median filter with a poorly chosen window size to a chromatogram peak.

The median filters used in step 26 have parameters that are adjusted to achieve optimal filtering of the signal. The moving median filter, for example, has one parameter, the window size, the number of points over which the median is computed. The optimal window size is determined by a number of factors including the typical peak width and the scan rate. The peak width of LC-MS or GC-MS data varies with column conditions, flow rate, and mobile and stationary phases, among other factors. The window size should not be wider than the typical peak width, or peaks will be significantly distorted. FIG. 5 illustrates the use of a moving median window that is larger than the peak width. As shown, the peak base is approximately five points wide, while the filter window is nine points wide. The peak is essentially removed, and so this filter width is unacceptable. The filter width must be decreased to three points before the peak can survive the filter substantially unchanged.

In addition, the scan rate determines the density of points in the chromatogram and therefore also affects the optimal window size. If scans are performed half as frequently as in the chromatogram of FIG. 3A, all else being equal, the peak contains fewer points and therefore a smaller window is needed to retain the peak while eliminating noise spikes. From the point of view of the present invention, therefore, it is desirable to scan more frequently, assuming the increased sampling does not result in degraded signal-to-noise ratios in the individual scans. In a preferred embodiment, the method derives an expected peak width from the chromatography parameters and resolution and then selects a window size based on the expected peak width.

Additionally, the optimal parameters are determined by the quality of the resulting reduced total ion chromatogram and the ease and accuracy with which subsequent component detection or automated peak picking can be performed.

In some embodiments, an adaptive window size is employed. The window size is not the same for all data points, but varies based on a number of factors. The window size can be selected based on characteristics of the data by analyzing subsets of points in each mass chromatogram. Alternatively, the variation in window size can be predetermined based on knowledge of the instrument conditions. If peaks at later retention times are known to be broader than peaks at earlier times, then the window is preset to increase with retention time.

Additional median filters include a modified median filter. This filter has more parameters than the moving median filter, but the parameters are optimized based on the same principles.

Methods of the invention preferably use standard algorithms for implementing the various steps. For example, the moving median filter is applied using existing techniques for obtaining the median of a set of points. In one such algorithm, the median window is applied sequentially to the data beginning at the lowest-time data point. Points within the window are ordered and the central point selected as the median. For subsequent points, the earliest-time point is removed and the new point inserted into the correct position in the ordered set. At the edges of the data set, additional points are appended so that the window can be centered on the first and last points. Preferably, the additional points have the same values as the edge points.

Figure 6A:
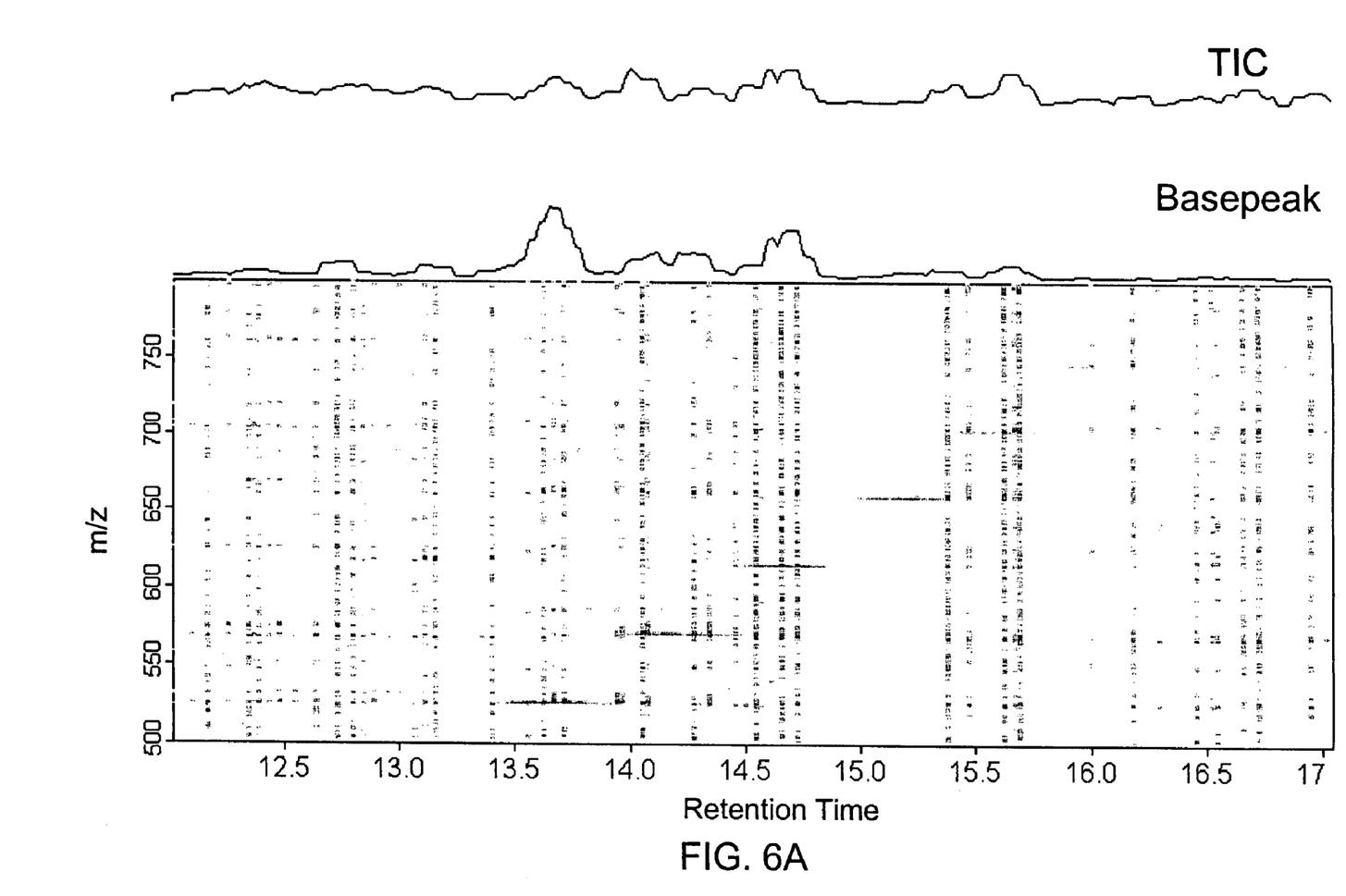
FIGS. 6A-6B show total ion chromatograms, base peak traces, and two-dimensional LC-MS data obtained from an LC-MS experiment of a proteolytic digest of human serum, before and after application of the moving median filter of the invention, respectively.
Figure 6B:
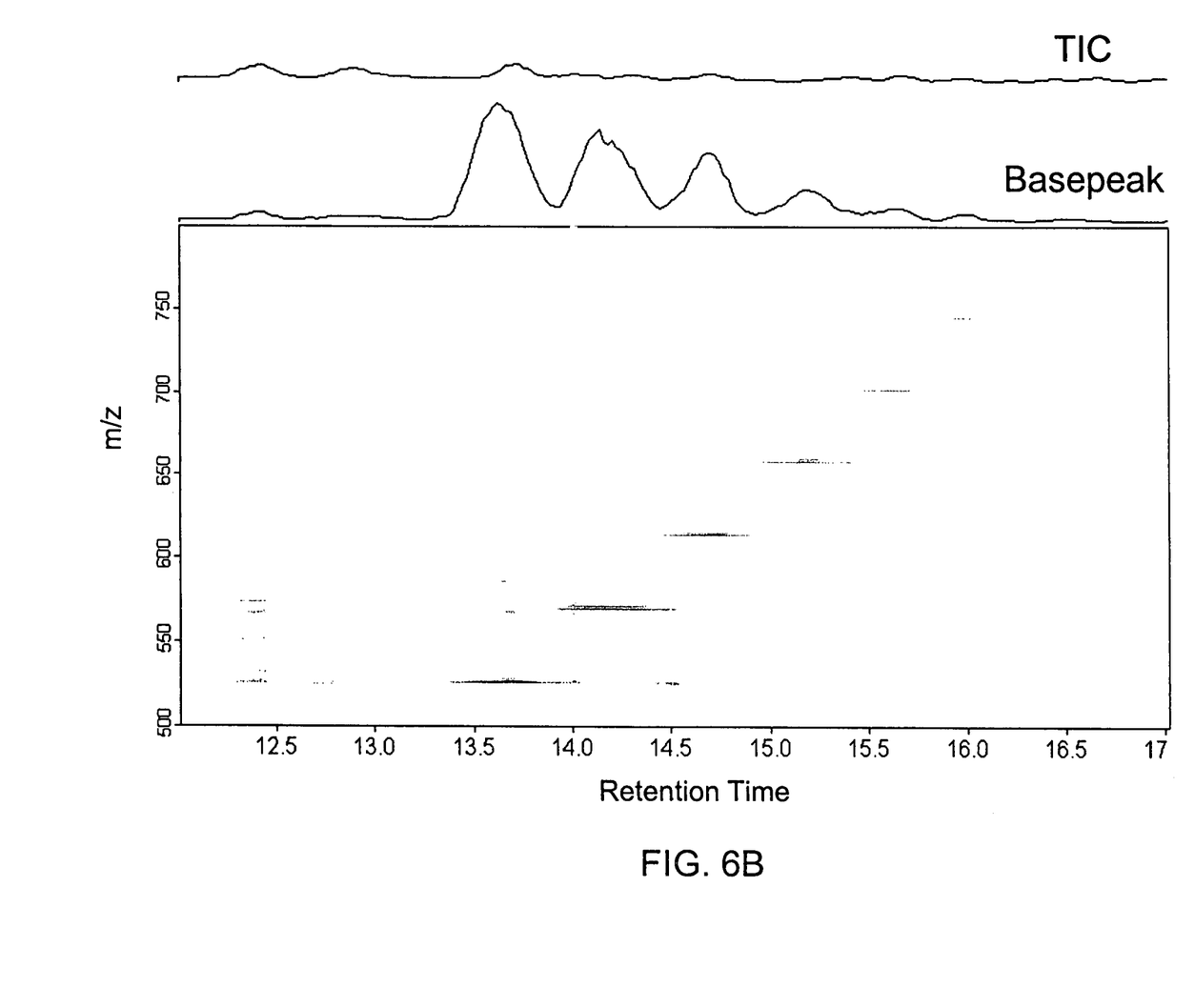
Figure 6C:
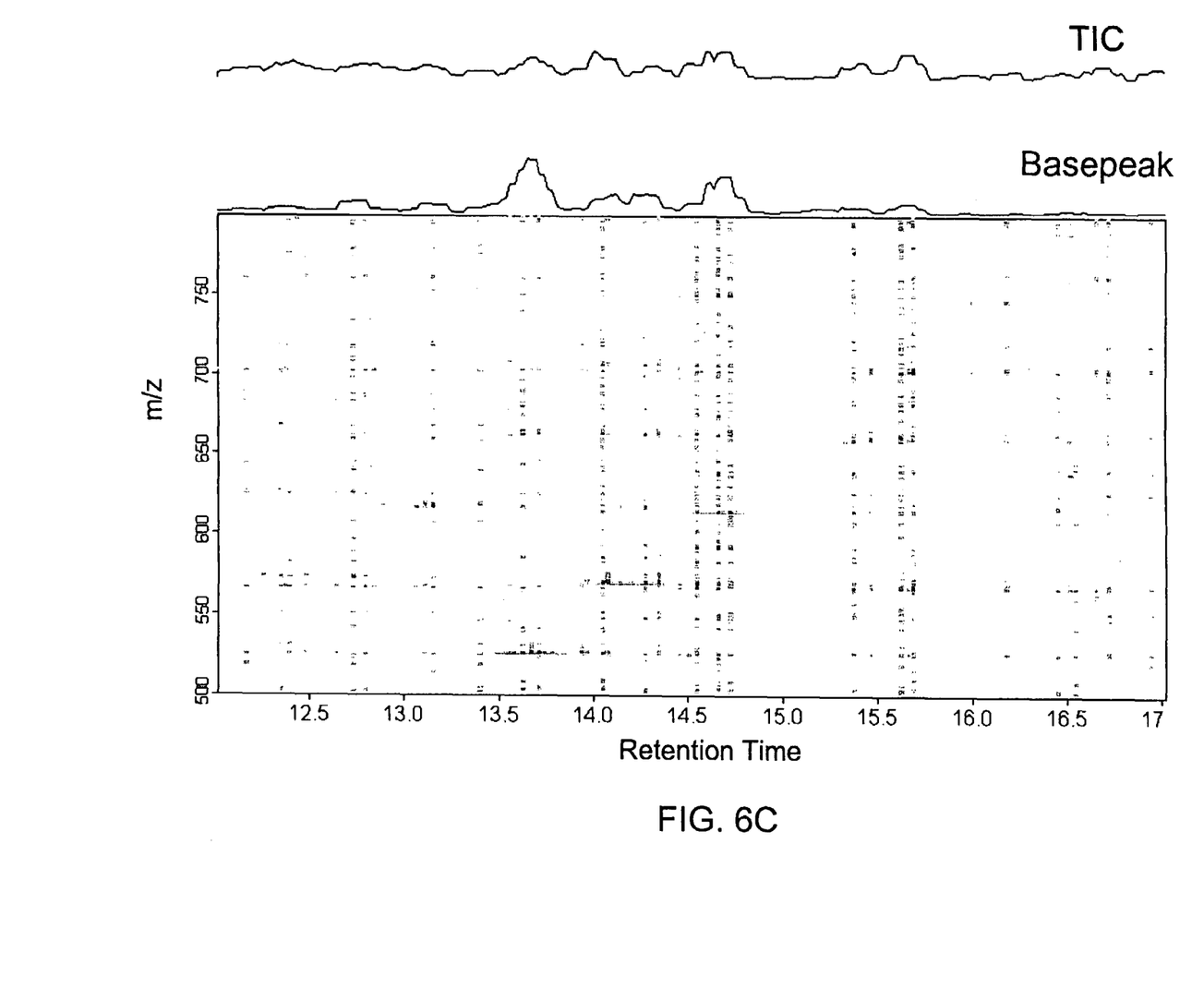
FIG. 6C shows the total ion chromatogram, base peak trace, and two-dimensional LC-MS plot of FIG. 6A after application of a mean filter.

An example application of the method is shown in FIGS. 6A and 6B. FIG. 6A shows a total ion current chromatogram, base peak trace, and two-dimensional plot acquired from an LC-MS experiment of a proteolytic digest of human serum. The darkness of each point in the two-dimensional plot corresponds to the detected intensity at that mass-to-charge ratio and retention time. Each point in the TIC is the sum of all points directly below it in the two-dimensional plot, while each point in the base peak trace is the maximum value of all points below it. A moving median filter with a window size of seven points was applied to the mass chromatograms extracted from the data. FIG. 6B shows the resulting filtered data. FIG. 6C shows the results of applying a seven-point mean filter to the same data. Note that the mean filter changes the data very little, while the median filter clearly brings out six smooth peaks.

Figure 7:
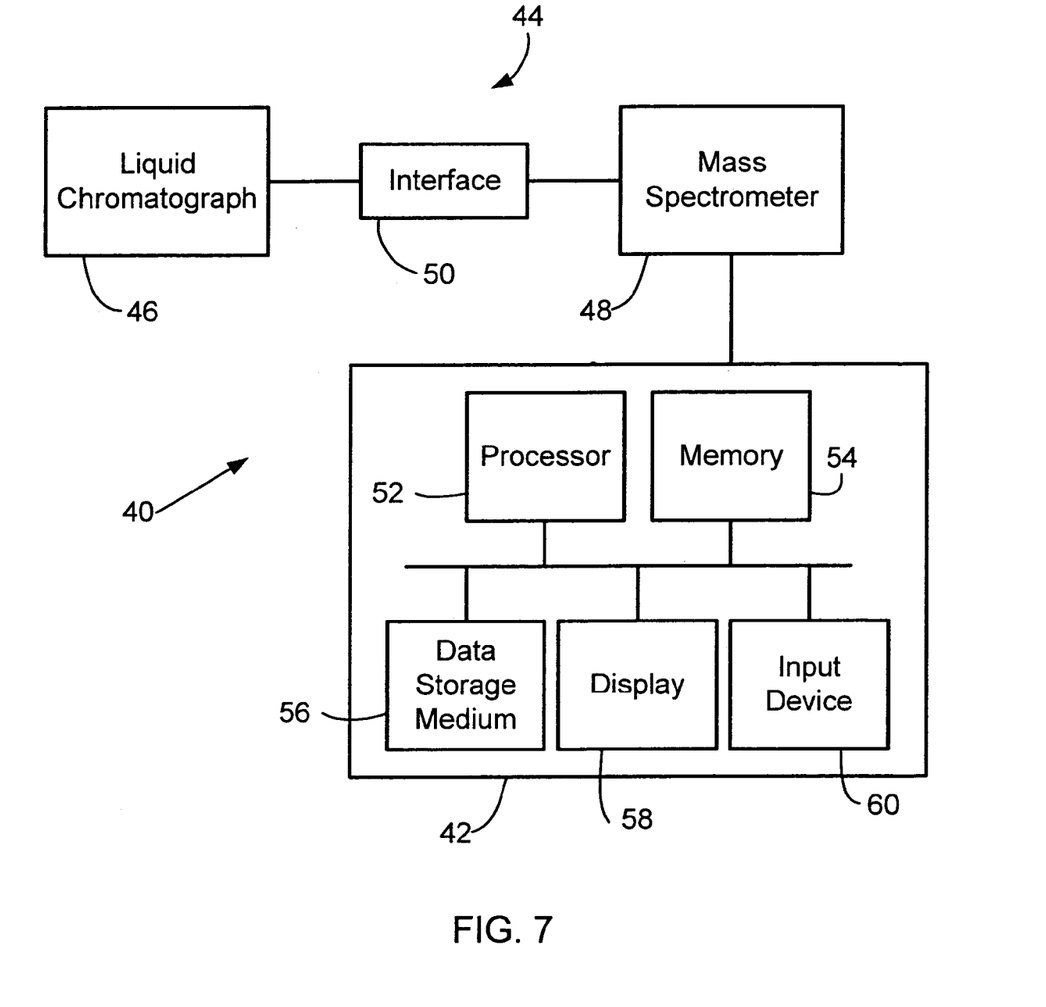
FIG. 7 is a block diagram of a hardware system for implementing the method of FIG. 4.

Although not limited to any particular hardware configuration, the present invention is typically implemented in software by a system 40, shown in FIG. 7, containing a computer 42 in communication with an analytical instrument, in this case a LC-MS instrument 44 that includes a liquid chromatography instrument 46 connected to a mass spectrometer 48 by an interface 50. The computer 42 acquires raw data directly from the instrument 44 via an analog-to-digital converter. Alternatively, the invention can be implemented by a computer in communication with an instrument computer that obtains the raw data. Of course, specific implementation details depend on the format of data supplied by the instrument computer. Preferably, the entire process is automated: the user sets the instrument parameters and injects a sample, the two-dimensional data are acquired, and the data are filtered for subsequent processing or transfer to a suitable database.

The computer 42 implementing the invention typically contains a processor 52, memory 54, data storage device 56, display 58, and input device 60. Methods of the invention are executed by the processor 52 under the direction of computer program code stored in the computer 42. Using techniques well known in the computer arts, such code is tangibly embodied within a computer program storage device accessible by the processor 52, e.g., within system memory 54 or on a computer readable storage medium 56 such as a hard disk or CD-ROM. The methods may be implemented by any means known in the art. For example, any number of computer programming languages, such as Java, C++, or LISP may be used. Furthermore, various programming approaches such as procedural or object oriented may be employed.

It is to be understood that the steps described above are highly simplified versions of the actual processing performed by the computer 42, and that methods containing additional steps or rearrangement of the steps described are within the scope of the present invention.

It should be noted that the foregoing description is only illustrative of the invention. Various alternatives and modifications can be devised by those skilled in the art without departing from the invention. Accordingly, the present invention is intended to embrace all such alternatives, modifications and variances which fall within the scope of the disclosed invention.

What is claimed is:

1. A method for characterizing a chemical sample, comprising:
    acquiring a series of mass spectra of said sample;
    generating a set of discrete data points based on the mass spectra, said data points comprising a plurality of chromatograms;
    selecting a data filter window size;
    centering said data filter window on one or more particular data points of said set of data points; and
    replacing said particular data point with the median of all points within said window to produce a filtered mass chromatogram.

2. The method of claim 1, further comprising:
    applying a component selection algorithm to said filtered mass chromatogram.

3. The method of claim 1, wherein said discrete data points correspond to integer mass values.

4. The method of claim 1, wherein said discrete data points correspond to non-integer mass values.

5. The method of claim 1, further comprising:
    combining a plurality of filtered mass chromatograms into a total ion current chromatogram.

6. The method of claim 5, wherein said combining comprises summing a plurality of intensities associated with said filtered mass chromatograms.

7. The method of claim 5, wherein said combining comprises thresholding said mass spectra using said plurality of filtered mass chromatograms.

8. The method of claim 1, wherein said data window filter size is selected based on at least one of:
    (a) being not wider than a typical data peak width;
    (b) a scan rate at which said generating is performed;
    (c) data characteristics obtained by analyzing subsets of points in said plurality of mass chromatograms; and
    (d) a predetermined knowledge of instrument conditions.

9. A program storage device accessible by a processor, tangibly embodying a program of instructions executable by said processor to perform method steps for a chemical sample analysis method, said method steps comprising:
    acquiring a series of mass spectra of said sample;
    generating a set of discrete data points based on the mass spectra, said data points comprising a plurality of chromatograms;
    selecting a data filter window size;
    centering said data filter window on one or more particular data points of said set of data points; and
    replacing said particular data point with the median of all points within said window to produce a filtered mass chromatogram.

10. The program storage device of claim 9, said method steps further comprising:
    applying a component selection algorithm to said filtered mass chromatogram.

11. The program storage device of claim 9, wherein said discrete data points correspond to integer mass values.

12. The program storage device of claim 9, wherein said discrete data points correspond to non-integer mass values.

13. The program storage device of claim 9, said method steps further comprising:
    combining a plurality of filtered mass chromatograms into a total ion current chromatogram.

14. The program storage device of claim 13, wherein said combining comprises summing a plurality of intensities associated with said filtered mass chromatograms.

15. The program storage device of claim 13, wherein said combining comprises thresholding said mass spectra using said plurality of filtered mass chromatograms.

16. The program storage device of claim 9, wherein said data window filter size is selected based on at least one of:
    (a) being not wider than a typical data peak width;
    (b) a scan rate at which said generating is performed;
    (c) data characteristics obtained by analyzing subsets of points in said plurality of mass chromatograms; and
    (d) a predetermined knowledge of instrument conditions.

17. A method of characterizing a chemical sample, comprising:
    obtaining a chromatogram from a series of mass spectra of said sample, wherein said mass spectra are generated by chromatography and mass spectrometry, and wherein said chromatogram comprises signal data and noise data; and
    applying a non-linear filter to said chromatogram to remove at least some of said noise data, thereby producing a filtered chromatogram.

18. The method of claim 17, wherein said chromatogram is a total ion chromatogram and said filtered chromatogram is a filtered total ion chromatogram.

19. The method of claim 18, further comprising generating individual chromatograms from said total ion chromatogram, wherein said non-linear is applied to said individual chromatograms.

20. The method of claim 17, wherein said chromatography is liquid chromatography.

* * * * *